(12) United States Patent
Ogino et al.

(10) Patent No.: US 7,309,488 B2
(45) Date of Patent: Dec. 18, 2007

(54) ADSORBENTS FOR DILATED CARDIOMYOPATHY

(75) Inventors: Eiji Ogino, Kobe (JP); Shigeo Furuyoshi, Kobe (JP); Fumiyasu Hirai, Amagasaki (JP); Takehiro Nishimoto, Osaka (JP)

(73) Assignee: Kaneka Corporation, Osaka (JP)

(*) Notice: Subject to any disclaimer, the term of this patent is extended or adjusted under 35 U.S.C. 154(b) by 654 days.

(21) Appl. No.: 10/221,042

(22) PCT Filed: Apr. 9, 2001

(86) PCT No.: PCT/JP01/03026

§ 371 (c)(1),
(2), (4) Date: Nov. 15, 2002

(87) PCT Pub. No.: WO01/76662

PCT Pub. Date: Oct. 18, 2001

(65) Prior Publication Data

US 2004/0120946 A1      Jun. 24, 2004

(30) Foreign Application Priority Data

Apr. 7, 2000     (JP)     ............................. 2000-106915

(51) Int. Cl.
*A61K 39/00* (2006.01)
*C07K 1/22* (2006.01)

(52) U.S. Cl. .................. 424/140.1; 530/413; 604/5.01; 604/5.02

(58) Field of Classification Search ............. 424/140.1; 436/506, 507, 518, 824; 530/341.1, 413; 604/5.01, 5.02
See application file for complete search history.

(56) References Cited

U.S. PATENT DOCUMENTS

| | | | | |
|---|---|---|---|---|
| 4,229,537 A | * | 10/1980 | Hodgins et al. | ............. 435/177 |
| 6,994,970 B1 | * | 2/2006 | Ronspeck et al. | ............. 435/6 |
| 7,022,322 B2 | * | 4/2006 | Koll et al. | ............... 424/140.1 |
| 2004/0120946 A1 | * | 6/2004 | Ogino et al. | ............. 424/140.1 |
| 2005/0271653 A1 | * | 12/2005 | Strahilevitz | .............. 424/140.1 |

FOREIGN PATENT DOCUMENTS

| | | |
|---|---|---|
| JP | 63-159753 | 7/1988 |
| JP | 11-001439 | 1/1999 |
| WO | WO 95/31727 | * 11/1995 |
| WO | WO 97/17980 | * 5/1997 |

OTHER PUBLICATIONS

Michael Liang-Xiong Fu, et al., "Functional Epitope Analysis of the Second Extracellular Loop of the Human Heart Muscarinic Acetylcholine Receptor", *Journal of Molecular and Cellular Cardiology*, vol. 27, 1995, pp. 427-436.

Wallukat, Gerd, et al., "Anti-$\beta_1$—Adrenoceptor Autoantibodies with Chronotropic Activity from the Serum of Patients with Dilated Cardiomyopathy: Mapping of Epitopes in the First and Second Extracellular Loops", *Journal of Molecular and Cellular Cardiology*, vol. 27, 1995, pp. 397-406.

Wallukat, Gerd, et al., "Agonistic Effects of Anti-Peptide Antibodies and Autoantibodies Directed Against Adrenergic and Cholinergic Receptors: Absence of Desensitization", *Blood Pressure*, vol. 5, Supp. 3, 1996, pp. 31-36.

Magnusson, Yvonne, Ph.D., et al., "Autoimmunity in Idiopathic Dilated Cardiomyopathy, Characterization of Antibodies Against the $B_1$ Adrenoceptor with Positive Chronotropic Effect", *Circulation*, vol. 89, No. 6, 1994, pp. 2760-2767.

* cited by examiner

*Primary Examiner*—David A. Saunders
(74) *Attorney, Agent, or Firm*—Kenyon & Kenyon LLP (57) ABSTRACT

An adsorbent which comprises a water-insoluble carrier and a compound, which is immobilized on said carrier, having a binding affinity for an antibody against $\beta 1$-adrenoceptor and/or an antibody against M2 muscarinic receptor exhibits a remarkably large adsorptive capacity.

11 Claims, 2 Drawing Sheets

SEQUENCE LISTING

```
<160> NUMBER OF SEQ ID NOS: 13

<210> SEQ ID NO 1
<211> LENGTH: 13
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                        antibody against beta1-adrenoceptor and/or an
                        antibody against M2 muscarinic receptor

<400> SEQUENCE: 1

Trp Gly Arg Trp Glu Tyr Gly Ser Phe Phe Cys Glu Leu
1               5                   10

<210> SEQ ID NO 2
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
```

```
                              antibody against beta1-adrenoceptor and/or an
                              antibody against M2 muscarinic receptor

<400> SEQUENCE: 2

Glu Tyr Gly Ser Phe Phe
1               5

<210> SEQ ID NO 3
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                              antibody against beta1-adrenoceptor and/or an
                              antibody against M2 muscarinic receptor

<400> SEQUENCE: 3

Ser Phe Phe Cys Glu Leu
1               5

<210> SEQ ID NO 4
<211> LENGTH: 23
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                              antibody against beta1-adrenoceptor and/or an
                              antibody against M2 muscarinic receptor

<400> SEQUENCE: 4

Arg Ala Glu Ser Asp Glu Ala Arg Arg Cys Tyr Asn Asp Pro Lys Cys
1               5                   10                  15
Cys Asp Phe Val Thr Asn Arg
            20

<210> SEQ ID NO 5
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                              antibody against beta1-adrenoceptor and/or an
                              antibody against M2 muscarinic receptor

<400> SEQUENCE: 5

Val Lys Ala Phe His Arg Glu Leu Val Pro Asp
1               5                   10

<210> SEQ ID NO 6
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                              antibody against beta1-adrenoceptor and/or an
                              antibody against M2 muscarinic receptor

<400> SEQUENCE: 6
```

```
Ala Arg Arg Cys Tyr Asn Asp
1               5

<210> SEQ ID NO 7
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                         antibody against beta1-adrenoceptor and/or an
                         antibody against M2 muscarinic receptor

<400> SEQUENCE: 7

Pro Lys Cys Cys Asp Phe
1               5

<210> SEQ ID NO 8
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                         antibody against beta1-adrenoceptor and/or an
                         antibody against M2 muscarinic receptor

<400> SEQUENCE: 8

Val Arg Thr Val Glu Asp Gly Glu Cys Tyr Ile Gln Phe Phe Ser Asn
1               5                   10                  15

Ala Ala Val Thr Phe Gly Thr Ala Ile
            20                  25

<210> SEQ ID NO 9
<211> LENGTH: 29
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                         antibody against beta1-adrenoceptor and/or an
                         antibody against M2 muscarinic receptor

<400> SEQUENCE: 9

His Trp Trp Arg Ala Glu Ser Asp Glu Ala Arg Arg Cys Tyr Asn Asp
1               5                   10                  15

Pro Lys Cys Cys Asp Phe Val Thr Asn Arg Gly Ala Cys
            20                  25

<210> SEQ ID NO 10
<211> LENGTH: 29
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                         antibody against beta1-adrenoceptor and/or an
                         antibody against M2 muscarinic receptor

<400> SEQUENCE: 10

Val Arg Thr Val Glu Asp Gly Glu Cys Tyr Ile Gln Phe Phe Ser Asn
```

-continued

```
                1               5                   10                  15
Ala Ala Val Thr Phe Gly Thr Ala Ile Pro Ala Lys Lys
                    20                  25

<210> SEQ ID NO 11
<211> LENGTH: 28
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
                        antibody against beta1-adrenoceptor and/or an
      antibody against M2 muscarinic receptor

<400> SEQUENCE: 11

His Trp Trp Arg Ala Glu Ser Asp Glu Ala Arg Arg Cys Tyr Asn Asp
1               5                   10                  15

Pro Lys Cys Cys Asp Phe Val Thr Asn Arg Ala Cys
            20                  25

<210> SEQ ID NO 12
<211> LENGTH: 26
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
      antibody against beta1-adrenoceptor and/or an
      antibody against M2 muscarinic receptor

<400> SEQUENCE: 12

Val Arg Thr Val Glu Asp Gly Glu Cys Tyr Ile Gln Phe Phe Ser Asn
1               5                   10                  15

Ala Ala Val Thr Phe Gly Thr Ala Ile Cys
            20                  25

<210> SEQ ID NO 13
<211> LENGTH: 18
<212> TYPE: PRT
<213> ORGANISM: Artificial
<220> FEATURE:
<223> OTHER INFORMATION: peptide
<220> FEATURE:
<221> NAME/KEY: MISC_FEATURE
<223> OTHER INFORMATION: Peptide having a binding affinity for an
      antibody against beta1-adrenoceptor and/or an
      antibody against M2 muscarinic receptor

<400> SEQUENCE: 13

Ser Phe Phe Cys Glu Leu Ala Asp Gly Tyr Pro Lys Cys Cys Asp Phe
1               5                   10                  15

Ala Cys
```

ADSORBENTS FOR DILATED CARDIOMYOPATHY

TECHNICAL FIELD

The present invention relates to an adsorbent designed to selectively remove an antibody against β1-adrenoceptor and/or an antibody against M2 muscarinic receptor by adsorption from a body fluid (e.g. blood, plasma, etc.) and thereby encourage the treatment of dilated cardiomyopathy (DCM) and other diseases in which an antibody against β1-adrenoceptor and/or an antibody against M2 muscarinic receptor is an exacerbating factor, an adsorption apparatus utilizing said adsorbent, and a method of adsorbing an antibody against β1-adrenoceptor and/or an antibody against M2 muscarinic receptor.

BACKGROUND ART

Dilated cardiomyopathy is a disease in which the contractility of the ventricular muscle is severely compromised to cause cardiac enlargement and, compared with hypertrophic cardiomyopathy, its prognosis is extremely poor. In Japan, persons surviving 5 years following the diagnosis reportedly account for about 50%. For the treatment of dilated cardiomyopathy, cardiac transplantation is preferably indicated as a radical treatment but since donations are outnumbered by cases on the waiting list, the symptomatic treatment of heart failure is a dominant treatment today. There are reported cases of improved cardiac function and prognosis following administration of an angiotensin-converting enzyme (ACE) inhibitor or a β-adrenergic blocker but the demand for efficacious therapeutic drugs and treatment is still outstanding.

Meanwhile, Matsui et al. reported that administration of a peptide derived from β1-adrenoceptor by addition of Cys to its second loop (His Trp Trp Arg Ala Glu Ser Asp Glu Ala Arg Arg Cys Tyr Asn Asp Pro Lys Cys Cys Asp Phe Val Thr Asn Arg Cys; SEQ ID NO:14) or a peptide derived from M2 muscarinic receptor by addition of Cys to its second loop (Val Arg Thr Val Glu Asp Gly Glu Cys Tyr Ile Gln Phe Phe Ser Asn Ala Ala Val Thr Phe Gly Thr Ala Ile Cys; SEQ ID NO:15) to rabbits resulted in the emergence of an antibody to each administered peptide and that the heart of rabbits that died 9 months later gave findings of dilated cardiomyopathy (Matsui S, Fu M L. Myocardial injury due to G-protein coupled receptor-autoimmunity. Jpn Heart J. 1998;39(3):261-74), thus suggesting that these antibodies act as etiologic factors in dilated cardiomyopathy. Further, Wallukat, G et al. purified an antibody against β1-adrenoceptor by using an adsorbent prepared by immobilizing the second-loop peptide of β1-adrenoceptor (His Trp Trp Arg Ala Glu Ser Asp Glu Ala Arg Arg Cys Tyr Asn Asp Pro Lys Cys Cys Asp Phe Val Thr Asn Arg; SEQ ID NO:16) on CNBr-activated Sepharose 4B (Wallukat G, Wollenberger A, Morwinski R, Pitschner H F. Anti-beta 1-adrenoceptor autoantibodies with chronotropic activity from the serum of patients with dilated cardiomyopathy: mapping of epitopes in the first and second extracellular loops. J Mol Cell Cardiol January 1995 ;27(1):397-406). However, they did not bring the serum directly into contact with the adsorbent. They first added a 40% saturated aqueous solution of ammonium sulfate to the serum to precipitate its immunoglobulin fraction (ammonium sulfate precipitation), redissolved the precipitate, dialyzed the solution, and thereafter performed a fractional purification with the adsorbent. This suggests that if the serum or the like in the state not pretreated (ammonium sulfate precipitation and dialysis) were brought into contact with the adsorbent they had synthesized, no sufficient selective adsorption should have been obtained.

SUMMARY OF THE INVENTION

In view of the above disadvantages, the present invention has for its object to provide an adsorbent for an antibody against β1-adrenoceptor and/or an antibody against M2 muscarinic receptor, which is capable of efficient and selective adsorption of an antibody against β1-adrenoceptor and/or an antibody against M2 muscarinic receptor occurring in a body fluid (e.g. blood, plasma or the like) without requiring a pretreatment (ammonium sulfate precipitation and dialysis) of the body fluid. A further object is to provide an adsorption apparatus utilizing this adsorbent and a method for adsorbing an antibody against β1-adrenoceptor and/or an antibody against M2 muscarinic receptor.

For accomplishing the above objects, the inventors of the present invention had tentatively conjugated various compounds to water-insoluble carriers in order to develop an adsorbent which, when contacted with the patient's blood, would exhibit a high adsorptive affinity for an antibody against β1-adrenoceptor and/or an antibody against M2 muscarinic receptor but would not simultaneously adsorb proteins such as albumin. As a result, we discovered that an adsorbent comprising a water-insoluble carrier and a compound, which is immobilized on said carrier, having a binding affinity for an antibody against β1-adrenoceptor and/or an antibody against M2 muscarinic receptor exhibits a remarkably large adsorptive capacity for an antibody against β1-adrenoceptor and/or an antibody against M2 muscarinic receptor, which finding having led to the accomplishment of the present invention.

The present invention, therefore, provides an adsorbent for an antibody against β1-adrenoceptor and/or an antibody against M2 muscarinic receptor which comprises a water-insoluble carrier, and a compound having a binding affinity for an antibody against β1-adrenoceptor and/or an antibody against M2 muscarinic receptor, and in which said compound is immobilized on the water-insoluble carrier.

The "compound having a binding affinity for an antibody against β1-adrenoceptor and/or an antibody against M2 muscarinic receptor" in the context of the present invention is a compound whose dissociation constant (KD) with an antibody against β1-adrenoceptor and/or an antibody against M2 muscarinic receptor is not more than $10^{-4}$ [M] (as measured with BIAcore, product of Pharmacia) or a compound which, when immobilized on a carrier in a proportion of not less than 0.00001 μmol but not more than 100 μmol per mL of the carrier to synthesize an adsorbent and the adsorbent thus constructed is contacted with a fluid containing said antibody for 2 hours (e.g. adsorbent:liquid=1:1 (v/v)), may reduce the concentration of the antibody by not less than 30%.

In a preferred embodiment, the compound having a binding affinity for an antibody against β1-adrenoceptor and/or an antibody against M2 muscarinic receptor is a peptide in adsorbing an antibody against β1-adrenoceptor and/or an antibody against M2 muscarinic receptor.

In a preferred embodiment, the compound having a binding affinity for an antibody against β1-adrenoceptor and/or an antibody against M2 muscarinic receptor is at least one peptide selected from the group consisting of

```
Trp Gly Arg Trp Glu Tyr Gly Ser Phe Phe Cys Glu Leu,    (SEQ ID NO:1)

Glu Tyr Gly Ser Phe Phe,                                 (SEQ ID NO:2)

Ser Phe Cys Glu Leu,                                     (SEQ ID NO:3)

Arg Ala Glu Ser Asp Glu Ala Arg Arg Cys Tyr Asn Asp Pro Lys,(SEQ ID NO:4)
Cys Cys Asp Phe Val Thr Asn Arg

Val Lys Ala Phe His Arg Glu Leu Val Pro Asp,             (SEQ ID NO:5)

Ala Arg Arg Cys Tyr Asn Asp,                             (SEQ ID NO:6)

Pro Lys Cys Cys Asp Phe                                  (SEQ ID NO:7)
and

Val Arg Thr Val Glu Asp Gly Glu Cys Tyr Ile Gln Phe Phe Ser,(SEQ ID NO:8)
Asn Ala Ala Val Thr Phe Gly Thr Ala Ile
``` fragment of at least one peptide selected from the group consisting of SEQ ID NO:1 to SEQ ID NO:8, or a peptide comprising at least one peptide and a fragment of at least one peptide selected from the group consisting of SEQ ID NO:1 to SEQ ID NO:8, in adsorbing an antibody against β1-adrenoceptor and/or an antibody against M2 muscarinic receptor.

In a preferred embodiment, the compound having a binding affinity for an antibody against β1-adrenoceptor and/or an antibody against M2 muscarinic receptor is at least one peptide selected from the group consisting of a peptide having $(Cys)_m$ or $(Lys)_n$, in which m and n each represents an integer of 0 to 10, at the N-terminus of said linear peptide and consisting of 0 to 20 amino acid residues and, a peptide having $(Cys)_p$ or $(Lys)_q$, in which p and q each represents an integer of 0 to 10, at the C-terminus of said linear peptide and consisting of 0 to 20 amino acid residues, in adsorbing an antibody against β1-adrenoceptor and/or an antibody against M2 muscarinic receptor.

In a preferred embodiment, the compound having a binding affinity for an antibody against β1-adrenoceptor and/or

```
X Trp Gly Arg Trp Glu Tyr Gly Ser Phe Phe Cys Glu Leu Y,  (SEQ ID NO:1a)

X Glu Tyr Gly Ser Phe Phe Y,                              (SEQ ID NO:2a)

X Ser Phe Phe Cys Glu Leu Y,                              (SEQ ID NO:3a)

X His Trp Trp Arg Ala Glu Ser Asp Glu Ala Arg Arg Cys Tyr (SEQ ID NO:4a)

Asn Asp Pro Lys Cys Cys Asp Phe Val Thr Asn Arg Y,

X Val Lys Ala Phe His Arg Glu Leu Val Pro Asp Y,          (SEQ ID NO:5a)

X Ala Arg Arg Cys Tyr Asn Asp Y,                          (SEQ ID NO:6a)

X Pro Lys Cys Cys Asp Phe Y,                              (SEQ ID NO:7a) and

X Val Arg Thr Val Glu Asp Gly Glu Cys Tyr Ile Gln Phe Phe (SEQ ID NO:8a)

Ser Asn Ala Ala Val Thr Phe Gly Thr Ala Ile Y,
``` in which X represents a peptide having $(Cys)_m$ or $(Lys)_n$, in which m and n each represents an integer of 0 to 10, at the N-terminus and consisting of 0 to 20 amino acid residues; Y represents a peptide having $(Cys)_p$ or $(Lys)_q$, in which p and q each represents an integer of 0 to 10, at the C-terminus and consisting of 0 to 20 amino acid residues, and the total number of the amino acid residues of X and Y is 1 to 40, in adsorbing an antibody against β1-adrenoceptor and/or an antibody against M2 muscarinic receptor.

In a preferred embodiment, the compound having a binding affinity for an antibody against β1-adrenoceptor and/or an antibody against M2 muscarinic receptor is a peptide comprising a linear peptide formed by coupling two or more peptides selected from the group consisting of SEQ ID NO:1 to SEQ ID NO:8 with a peptide of not more than 10 amino acid resides and, an antibody against M2 muscarinic receptor is immobilized on a water-insoluble carrier in a proportion of 0.00001 μmol to 100 μmol per mL of the carrier.

In a preferred embodiment, the water-insoluble carrier is porous in adsorbing an antibody against β1-adrenoceptor and/or an antibody against M2 muscarinic receptor.

In a preferred embodiment, in case said water-insoluble carrier is porous in adsorbing an antibody against β1-adrenoceptor and/or an antibody against M2 muscarinic receptor, the molecular weight exclusion limit of said carrier is 150,000 to 10,000,000.

In a preferred embodiment, the water-insoluble carrier is a hydrophilic carrier in adsorbing an antibody against β1-adrenoceptor and/or an antibody against M2 muscarinic receptor.

In a preferred embodiment, the adsorbent of the invention is used for adsorbing an antibody against β1-adrenoceptor and/or an antibody against M2 muscarinic receptor occurring in a body fluid.

In a preferred embodiment, the adsorbent of the invention is used for adsorbing an immunocomplex comprising an antibody against β1-adrenoceptor and/or an antibody against M2 muscarinic receptor occurring in a body fluid as a component.

The apparatus for adsorbing an antibody against β1-adrenoceptor and/or an antibody against M2 muscarinic receptor according to the invention comprises a housing equipped with a liquid inlet and a liquid outlet and packed with the adsorbent described in any of the above paragraphs and a means for preventing emigration of said adsorbent from said housing.

DETAILED DISCLOSURE OF INVENTION

The embodiments of the invention are now described, it being, however, to be understood that the present invention is by no means delimited in scope by the following description. The compound having a binding affinity for an antibody against β1-adrenoceptor and/or an antibody against M2 muscarinic receptor for use in the present invention is a compound which is substantially capable of adsorbing an antibody against β1-adrenoceptor and/or an antibody against M2 muscarinic receptor and, as such, is not limited to any specific compound but is preferably a substance which will specifically bind to the epitope (that is to say Fab) of the antibody against β1-adrenoceptor and/or the antibody against M2 muscarinic receptor. The following are representative examples.

```
Trp Gly Arg Trp Glu Tyr Gly Ser Phe Phe Cys Glu Leu,         (SEQ ID NO:1)

Glu Tyr Gly Ser Phe Phe,                                     (SEQ ID NO:2)

Ser Phe Phe Cys Glu Leu,                                     (SEQ ID NO:3)

Arg Ala Glu Ser Asp Glu Ala Arg Arg Cys Tyr Asn Asp Pro Lys  (SEQ ID NO:4)

Cys Cys Asp Phe Val Thr Asn Arg,

Val Lys Ala Phe His Arg Glu Leu Val Pro Asp,                 (SEQ ID NO:5)

Ala Arg Arg Cys Tyr Asn Asp,                                 (SEQ ID NO:6)

Pro Lys Cys Cys Asp Phe,                                     (SEQ ID NO:7)

Val Arg Thr Val Glu Asp Gly Glu Cys Tyr Ile Gln Phe Phe Ser  (SEQ ID NO:8)

Asn Ala Ala Val Thr Phe Gly Thr Ala Ile,

X Trp Gly Arg Trp Glu Tyr Gly Ser Phe Phe Cys Glu Leu Y,     (SEQ ID NO:1a)

X Glu Tyr Gly Ser Phe Phe Y,                                 (SEQ ID NO:2a)

X Ser Phe Phe Cys Glu Leu Y,                                 (SEQ ID NO:3a)

X His Trp Trp Arg Ala Glu Ser Asp Glu Ala Arg Arg Cys Tyr    (SEQ ID NO:4a)

Asn Asp Pro Lys Cys Cys Asp Phe Val Thr Asn Arg Y,

X Val Lys Ala Phe His Arg Glu Leu Val Pro Asp Y,             (SEQ ID NO:5a)

X Ala Arg Arg Cys Tyr Asn Asp Y,                             (SEQ ID NO:6a)

X Pro Lys Cys Cys Asp Phe Y                                  (SEQ ID NO:7a)
and

X Val Arg Thr Val Glu Asp Gly Glu Cys Tyr Ile Gln Phe Phe    (SEQ ID NO:8a)

Ser Asn Ala Ala Val Thr Phe Gly Thr Ala Ile Y,
``` in which X represents a peptide having $(Cys)_m$ or $(Lys)_n$ (m and n each represents an integer of 0 to 10) at the N-terminus and consisting of 0 to 20 amino acid residues; Y represents a peptide having $(Cys)_p$ or $(Lys)_q$ (p and q each represents an integer of 0 to 10) at the C-terminus and consisting of 0 to 20 amino acid residues; the total number of amino acid residues of X and Y is 1 to 40.

The water-insoluble carrier for use in the present invention includes inorganic carriers such as glass beads and silica gel, organic carriers such as synthetic polymers, e.g. crosslinked poly(vinyl alcohol), crosslinked polyacrylates, crosslinked polyacrylamide, crosslinked polystyrene, etc., and polysaccharides, e.g. crystalline cellulose, crosslinked cellulose, crosslinked agarose, crosslinked dextran, etc., The method of adsorbing an antibody against β1-adrenoceptor and/or an antibody against M2 muscarinic receptor according to the present invention comprises a step of contacting the adsorbent described in any of the above paragraphs with a liquid containing an antibody against β1-adrenoceptor and/or an antibody against M2 muscarinic receptor.

In a preferred embodiment, the above liquid containing an antibody against β1-adrenoceptor and/or an antibody against M2 muscarinic receptor is a body fluid.

As used in this specification, the term "body fluid" means blood, plasma, serum, ascites fluid, lymph, and intraarticular fluid, any fraction thereof, and any other liquid component derived from a living body.

composite carriers such as organic-organic and organic-inorganic carriers derived from various combinations of said carriers. Among these, hydrophilic carriers are particularly preferred because of highly selective adsorptive affinities for an antibody against β1-adrenoceptor and/or an antibody against M2 muscarinic receptor with comparatively less nonspecific adsorption. The hydrophilic carriers mentioned above mean carriers such that when the compound constituting a particular carrier is formed into a flat sheet, it shows a contact angle of not more than 60 degrees with respect to water. As representative carriers satisfying this condition, there can be mentioned carriers composed of polysaccharides such as cellulose, chitosan and dextran; poly(vinyl alcohol), saponified ethylene-vinyl acetate copolymer, polyacrylamide, polyacrylic acid, polymethacrylic acid, poly (methyl methacrylate), polyacrylic acid-grafted polyethylene, polyacrylamide-grafted polyethylene, glass, and so on.

As commercial products, GCL2000m, which is a porous cellulose gel, and Eupergit C 250 L, which is an epoxy-activated polymethacrylamide, among others, can be mentioned. It should, however, be understood that the carrier for use in the present invention is not limited to such specific carriers or activated carriers, of course. The above carriers may be used each independently or in an optional combination of two or more species. Furthermore, in view of the object and method of use of the adsorbent, the water-insoluble carrier for use in the present invention is preferably a carrier having a large surface area, that is to say a porous carrier having a multiplicity of pores of appropriate size.

When the water-insoluble carrier for use in the present invention is porous, its molecular weight exclusion limit is preferably 150,000 to 10,000,000. The molecular weight of an antibody against β1-adrenoceptor and/or an antibody against M2 muscarinic receptor is 140,000 to 1,000,000 and, therefore, in order that such antibody molecules may be adsorbed on a porous carrier with good efficiency, the size of molecular weight exclusion limit of the carrier is preferably larger than the diameter of the antibody molecules. However, if it is too large, the strength of the carrier will be reduced and the surface area also decreased. Therefore, it is preferable to use a carrier having a molecular weight exclusion limit of 250,000 to 5,000,000.

Referring, now, to the porous structure of the carrier, in consideration of the adsorptive capacity per unit volume of the carrier, total porosity is preferred to surface porosity and it is preferable to use a carrier having a pore volume of not less than 20% and a specific surface area of not less than 3 $m^2/g$.

In regard of the form of the carrier, any of bead form, fibrous form, membranous form (inclusive of hollow fiber) and other forms can be used and optionally selected but in consideration of the flow kinetics of body fluids during extracorporeal circulation, the bead form is particularly preferred. Beads having an average particle diameter of 10 to 2,500 μm are easy to use and the range of 25 μm to 800 μm is preferred.

Furthermore, the presence of a functional group which can be utilized for immobilizing a ligand on the surface of the carrier is favorable for the immobilization of the ligand. As representative examples of said functional group, hydroxyl, amino, aldehyde, carboxyl, thiol, silanol, amido, epoxy, succinylimido, acid anhydride group, etc. can be mentioned.

Furthermore, the carrier which can be used in the present invention includes both a rigid carrier and a soft carrier but for use as the carrier of an adsorbent for extracorporeal circulation treatment, it is an important requisite that there will be no plugging when, for example, a column is packed with it and a fluid is passed through it. For this purpose, sufficient mechanical strength is required of the carrier. Therefore, the carrier for use in the practice of the present invention is more preferably a rigid carrier. As used in this specification, the term "rigid carrier" means such a carrier, taking the case where it is a granular gel as an example, that when a cylindrical glass column (9 mm in. dia., column length 150 mm) is uniformly packed with the gel and an aqueous fluid is passed through the packed column under the following conditions, a linear correlation is obtained between pressure loss ΔP and flow rate up to 0.3 $kg/cm^2$.

Figure 1:
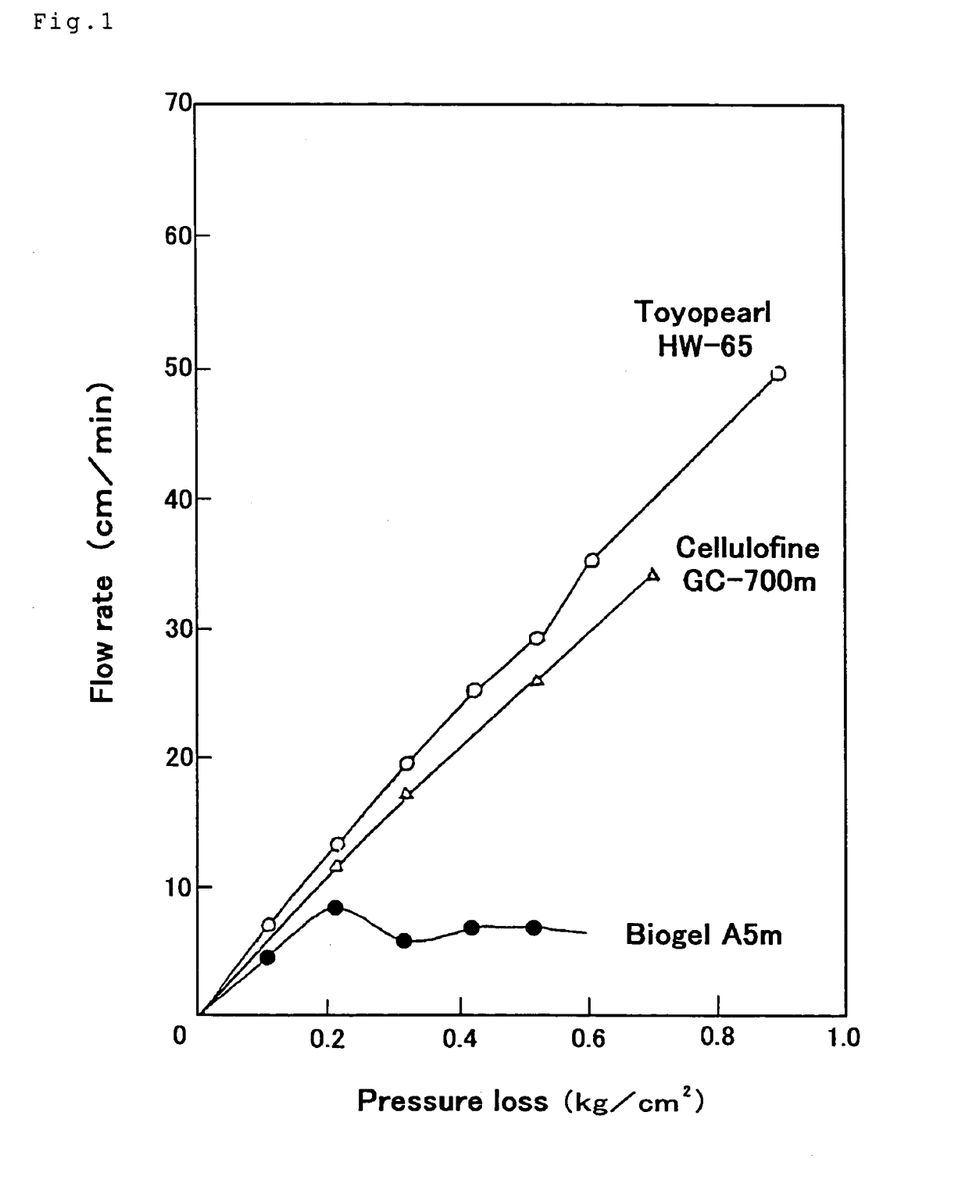
FIG. 1 is a graph of the relation between flow rate and pressure loss as studied using 3 different gels.

Thus, for example, cylindrical glass columns (9 mm in. dia., column length 150 mm), each fitted with a 15 μm-pore filter at either end, were uniformly packed with agarose gel (Biogel-A5m, particle size of 50 to 100 mesh, product of Bio-Rad), vinyl polymer gel (Toyopearl HW-65, particle size of 50 to 100 μm, product of Toyo Soda) and cellulose gel (Cellulofine GC-700m, particle size of 45 to 105 μm, product of Chisso Corporation), respectively, and using a peristatic pump, water was passed through each packed column to determine the relation between flow rate and pressure loss ΔP (FIG. 1). The flow rate (cm/min) was plotted on the ordinate and the pressure loss ($kg/cm^2$) on the abscissa. On the drawing, ○ represents Toyopearl HW-65, Δ represents Cellulofine GC-700m, and ● represents Biogel-A5m. It can be seen that whereas increasing the pressure results in a nearly proportional increase in flow rate in the cases of Toyopearl HW-65 and Cellulofine GC-700m, compaction took place in the case of Biogel-A5m so that increasing the pressure does not lead to an increase in flow rate.

In immobilizing a compound having a binding affinity for an antibody against β1-adrenoceptor and/or an antibody against M2 muscarinic receptor on said carrier, it is more preferable to carry out the immobilization via a hydrophilic spacer for minimizing the steric hindrance on said compound to improve the adsorption efficiency and suppressing nonspecific adsorption. As the hydrophilic spacer, a polyalkylene oxide derivative having a carboxyl, amino, aldehyde, epoxy or the like substituent group at either terminus, for instance, can be used with advantage.

The method for immobilizing said compound having a binding affinity for an antibody against β1-adrenoceptor and/or an antibody against M2 muscarinic receptor and an organic compound serving as the spacer is not particularly restricted but includes the techniques which are generally used in the immobilization of a protein or peptide on a carrier, for example the epoxy reaction, nick base reaction, condensation reaction using a carbodiimide reagent, active ester reaction, and carrier crosslinking reaction using a glutaraldehyde reagent, among others. However, in consideration of the fact that the adsorbent may be used for extracorporeal circulation treatment and hemocatharsis, it is preferable to apply an immobilization method such that the protein or the like will not readily be detached from the carrier in sterilization of the adsorbent or during a treatment session. For example, there may be mentioned (1) the technique which comprises causing the carboxyl group of a carrier to react with N-hydroxysuccinimide to form a succinimidooxycarbonyl group and, then, causing it to react with the amino group of a protein or peptide (active ester method), (2) the technique which comprises causing the amino or carboxyl group of a carrier to undergo condensation reaction with the carboxyl or amino group of a protein or peptide in the presence of a condensation reagent such as dicyclohexylcarbodiimide (condensation method), and (3) the technique which comprises crosslinking a protein or peptide using a compound having two or more functional groups, such as glutaraldehyde (carrier crosslinking method). To minimize the detachment and release of the protein or the like, the mode of coupling is preferably covalent binding.

Many different methods are available for contacting the carrier supporting the compound having a binding affinity for an antibody against β1-adrenoceptor and/or an antibody against M2 muscarinic receptor with a body fluid such as blood, plasma or serum to adsorb an antibody against β1-adrenoceptor and/or an antibody against M2 muscarinic receptor occurring in the body fluid. Among representative methods are (1) the method which comprises withdrawing a body fluid, pooling it in a bag or the like, admixing it with the adsorbent to adsorb an antibody against β1-adrenoceptor and/or an antibody against M2 muscarinic receptor, and filtering off the adsorbent to give a body fluid deprived of the antibody against β1-adrenoceptor and/or the antibody against M2 muscarinic receptor and (2) the method which comprises packing a vessel equipped with an inlet and an outlet, as well as a filter which allows passage of the body fluid but does not allow passage of the adsorbent at said outlet, with the adsorbent and passing the body fluid through the vessel. Whichever of these methods may be used, however, the latter method is not only simple procedure-wise but also capable of removing the antibody against β1-adrenoceptor and/or the antibody against M2 muscarinic receptor from a patient's body fluid with good efficiency on line when the vessel is integrated into an extracorporeal circulation circuit and, therefore, is suitable for the adsorbent of the present invention.

Figure 2:
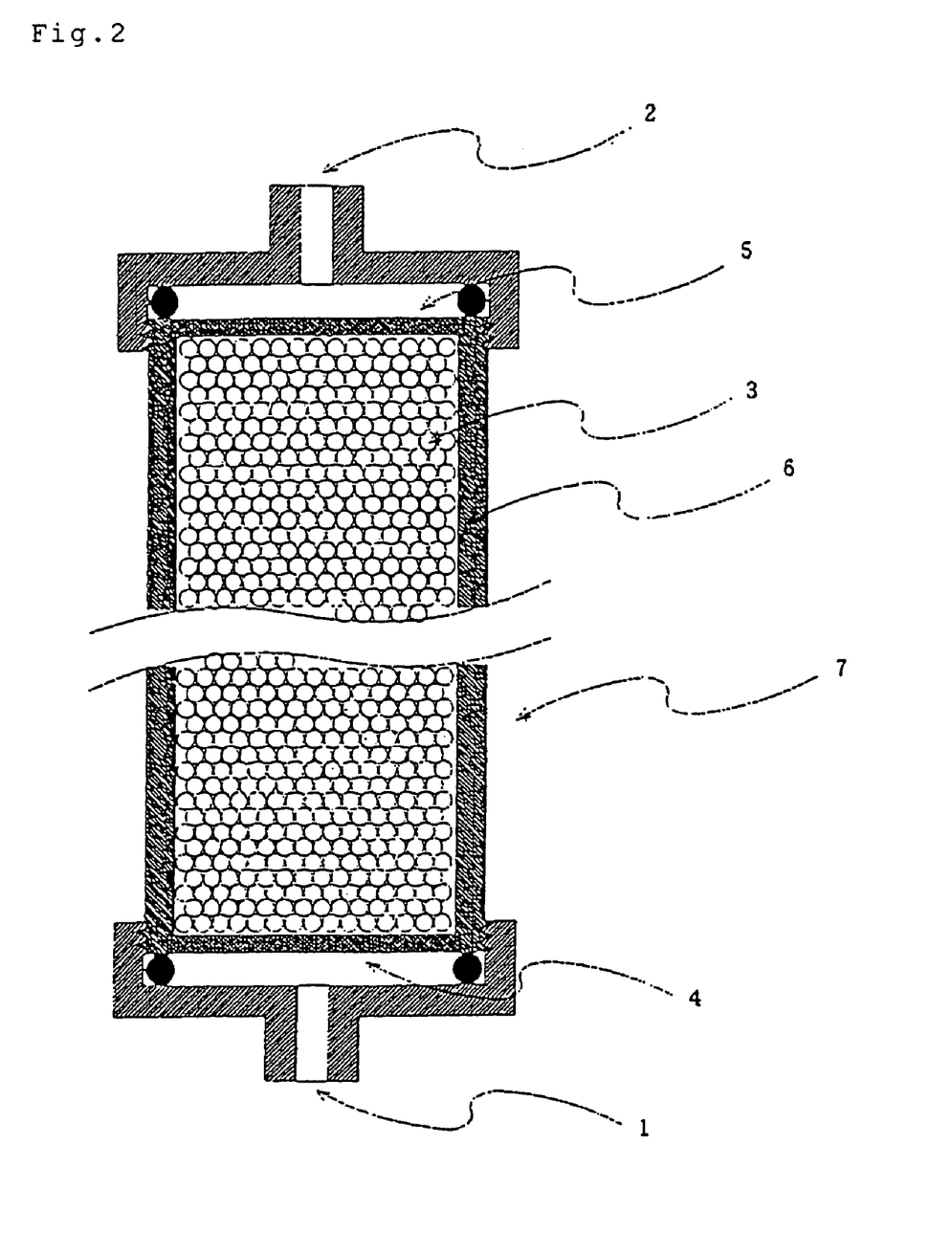
FIG. 2 is a schematic cross-section view showing an example of the adsorption apparatus for adsorbing an antibody against β1-adrenoceptor and/or an antibody against M2 muscarinic receptor according to the present invention.

Then, the adsorption apparatus for adsorbing an antibody against β1-adrenoceptor and/or an antibody against M2 muscarinic receptor according to the present invention which employs the adsorbent for an antibody against β1-adrenoceptor and/or an antibody against M2 muscarinic receptor is now described, with the schematic cross-section view thereof.

Referring to FIG. 2, the vessel 7 comprises a liquid inlet (or a liquid outlet) 1, a liquid outlet (or a liquid inlet) 2, the adsorbent 3 for an antibody against β1-adrenoceptor and/or an antibody against M2 muscarinic receptor according to the present invention, adsorbent emigration preventing means 4 and 5 which allow passage of a liquid and components of the liquid but does not allow passage of the adsorbent for an antibody against β1-adrenoceptor and/or an antibody against M2 muscarinic receptor, and a column 6. The geometry and material of the vessel are not particularly restricted but is preferably a cylindrical vessel having a capacity of about 20 to 400 ml, for instance, and a diameter of about 2 to 10 cm, for instance.

EXPLANATION OF NUMERALS

1: a body fluid inlet
2: a body fluid outlet
3: an adsorbent for an antibody against β1-adrenoceptor and/or an antibody against M2 muscarinic receptor
4,5: filters which allow passage of a body fluid and components of the body fluid but do not allow passage of the adsorbent for an antibody against β1-adrenoceptor and/or an antibody against M2 muscarinic receptor.
6: a column
7: an adsorption apparatus

BEST MODE FOR CARRYING OUT THE INVENTION

The following examples illustrate the present invention in further detail without defining the scope of the invention. It should also be understood that in this specification, various amino acid residues are indicated by the following abbreviations: Ala: L-alanine residue, Asp: L-aspartic acid residue, Asn: L-asparagine residue, Cys: L-cysteine residue, Gln: L-glutamine residue, Glu: L-glutamic acid residue, Gly: L-glycine residue, Ile: L-isoleucine residue, Leu: L-leucine residue, Lys: L-lysine residue, Phe: L-phenylalanine residue, Thr: L-threonine residue, Trp: L-tryptophan residue, Tyr: L-tyrosine residue, Val: L-valine residue. Furthermore, in this specification, the amino acid sequence of any peptide is shown in the conventional manner, i.e. the amino terminus (hereinafter N-terminus) at the left-hand side and the carboxyl terminus (hereinafter C-terminus) at the right-hand side.

EXAMPLE 1

1-1. Synthesis of a Peptide (SEQ ID NO:4)

The following peptide was synthesized by the solid-phase method using Peptide Synthesizer Model 4170 (manufactured by Pharmacia LKB).

```
Arg Ala Glu Ser Asp Glu Ala Arg Arg    (SEQ ID NO:4)
Cys Tyr Asn Asp Pro Lys Cys Cys Asp
Phe Val Thr Asn Arg
```

From among the Fmoc-protected amino acids in routine use, i.e. Fmoc-Ala, Fmoc-Arg, Fmoc-Asn(Trt), Fmoc-Asp (OtBu), Fmoc-Cys(Trt), Fmoc-Gln(Trt), Fmoc-Glu(OtBu), Fmoc-Gly, Fmoc-His, Fmoc-Ile, Fmoc-Leu, Fmoc-Lys (Boc), Fmoc-Met, Fmoc-Phe, Fmoc-Pro, Fmoc-Ser, Fmoc-Thr(tBu), Fmoc-Trp, Fmoc-Tyr(tBu), and Fmoc-Val, the Fmoc amino acids necessary for construction of the sequence were selected and, based on the substrate, 5 equivalents each were used. (In the above representation, Trt, OtBu, Boc, and tBu represent trityl, tert-butyl ester, tert-butyloxycarbonyl, and o-tert-butyl group, respectively).

After completion of the synthetic reaction, the product was washed on a glass filter serially with tert-amyl alcohol, acetic acid, and diethyl ether and dried in vacuo. To 1 g of the support obtained, 20 ml of trifluoroacetic acid (briefly, TFA), 260 µl of 1,2-ethanedithiol, and 780 µl of anisole were added and the mixture was stirred at room temperature for 1.5 hours and then filtered through a glass filter. The filtrate was concentrated under reduced pressure. The concentrate was then reprecipitated from anhydrous diethyl ether and the crudely purified peptide was recovered. This crudely purified peptide was dissolved in 0.1% TFA and purified by HPLC using a reversed-phase column (µBondasphere C18: product of Nippon Millipore Waters).

1-2. Synthesis of an Adsorbent (GCL2000m-SEQ ID NO:4)

1-2-1. Epoxy-Activation of GCL2000m

To 90 ml of the cellulosic porous hard gel GCL-2000m (product of Chisso Corporation; spherical protein molecular weight exclusion limit of 3,000,000) was added sufficient water to make 180 ml, followed by addition of 60 ml of 2M sodium hydroxide, and the temperature was adjusted to 40° C. To this was added 21 ml of epichlorohydrin, and the reaction was carried out at 40° C. with stirring for 1 hour. After completion of the reaction, the product was rinsed with water thoroughly to give an epoxy-activated cellulose gel.

1-2-2. Immobilization of the Peptide (SEQ ID NO:4)

In 0.5 mL of 0.05 M borate buffer (pH 10.0) was dissolved 0.5 mg of the peptide (SEQ ID NO:4) synthesized under 1-1., and the solution was readjusted to pH 10 and made up to 1.0 mL(peptide solution) by adding 0.01 N aqueous sodium hydroxide solution. This peptide solution was added to 0.4 mL of the above epoxy-activated GCL2000m and the mixture was shaken at 37° C. for 16 hours. The product was washed with a sufficient quantity of PBS (10 mM phosphate buffer containing 150 mM sodium chloride) to give GCL2000m-SEQ ID NO:4.

The peptide concentration of the reaction mixture was measured by HPLC immediately before immobilizing reaction and immediately after the reaction and the reaction rate was calculated to obtain immobilization rate. As a result, 0.8 mg (0.8 mg/mL, 0.25 μmol/ml) of the peptide was found to have been immobilized per mL of GCL2000m-SEQ ID NO:4.

1-3. Evaluation of the Adsorbent

To 50 μL of the GCL2000m-SEQ ID NO:4 synthesized under 1-2. was added 300 μL of serum A from an antibody against β1-adrenoceptor-positive (briefly, β1AR-Ab(+)) DCM patient, and after shaking at 37° C. for 2 hours, the value of the antibody against β1-adrenoceptor of the supernatant was determined by ELISA. A solution (50 μg/mL) of the β1-adrenoceptor second loop (β1AR2nd) peptide (See Comparative Example 1 (1)-1. for the method of synthesis), 50 μL, was added to an ELISA plate which was then allowed to stand at 4° C. overnight. After the plate was washed, 100 μL of skim milk (product of Difco) solution was added and the plate was allowed to stand at room temperature for 1 hour. After the plate was washed, 50 μL of a sample (a 10-fold dilution of said supernatant) was added and the plate was allowed to stand at 4° C. overnight. After the plate was washed, 50 μL of a biotin-labeled anti-human IgG antibody (product of Southern Biotechnology) solution was added and the plate was allowed to stand at room temperature for 1 hour. After the plate was washed, 50 μL of a streptavidin-peroxidase polymer (product of Sigma) solution was added and the plate was allowed to stand at room temperature for 1 hour. After the plate was washed, 100 μL of substrate solution was added and the plate was allowed to stand at room temperature for 30 minutes. The absorbance was then measured at 405 nm. From the absorbance found by using the DCM patient serum A (corresponding to 0% adsorption) in lieu of the above sample and the absorbance found by using healthy human serum (β1AR-Ab(−))(corresponding to 100% adsorption), the adsorptive capacity of GCL2000m-SEQ ID NO:4 was calculated (See Table 1 for the result).

COMPARATIVE EXAMPLE 1

(1)-1. Peptide (β1AR2nd)

For performance comparison with the adsorbent used by Wallukat et al., the following peptide, the second loop of β1-adrenoceptor (β1AR2nd), was synthesized in exactly the same way as described in Example 1 (1-1.).
His Trp Trp Arg Ala Glu Ser Asp Glu Ala
Arg Arg Cys Tyr Asn Asp Pro Lys Cys Cys
Asp Phe Val Thr Asn Arg (SEQ ID NO:16)

(1)-2. Synthesis of an Adsorbent (Sepharose 4B-β1AR2nd)

CNBr-activated Sepharose 4B (product of Pharmacia LKB; spherical protein molecular weight exclusion limit >20,000,000) was swollen with a small quantity of 1 mM HCl/H$_2$O solution for 15 minutes, washed with 1 mM HCl/H$_2$O solution, and further washed with coupling buffer (pH 8.3 0.5 M sodium chloride 0.1 M NaHCO$_3$). In 1 mL of coupling buffer was dissolved 0.5 mg of the peptide (β1AR2nd) synthesized under 2-1., and the solution was mixed with 0.4 mL of the pretreated CNBr-activated Sepharose 4B to carry out the reaction at 4° C. for 16 hours. After washing with coupling buffer, blocking buffer (pH 8.3 0.2 M glycine 0.5 M sodium chloride 0.1 M NaHCO$_3$) was added and the reaction was carried out at room temperature for 2 hours. The reaction product was washed alternately with two kinds of after-treating buffers (pH 4.0 0.5 M sodium chloride 0.1 M acetic acid-sodium acetate buffer; pH 8.0 0.5 M sodium chloride 0.1 M Tris-HCl buffer) for 3 times each to give Sepharose 4B-β1AR2nd.

The immobilization rate determined as under 1-2-2. was 1 mg/mL (0.27 μmol/ml) for Sepharose 4B-β1AR2nd. (Wallukat G, Wollenberger A, Morwinski R, Pitschner H F. Anti-beta 1-adrenoceptor autoantibodies with chronotropic activity from the serum of patients with dilated cardiomyopathy: mapping of epitopes in the first and second extracellular loops. J Mol Cell Cardiol January 1995;27(1):397-406).

(1)-3. Evaluation of the Adsorbent

Except that Sepharose 4B-β1AR2nd was used in lieu of the GCL2000m-SEQ ID NO:4 used in Example 1 (1-3.), the adsorption experiment using DCM patient serum A and ELISA were performed in otherwise the same manner as in Example 1 (1-3.), and the absorbance measurement and adsorption affinity calculation were carried out (See Table 1 for the result).

EXAMPLE 2

2-1. The Following Peptide (SEQ ID NO:9) was Synthesized in Exactly the Same Manner as Described in Example 1 (1-1.).

His Trp Trp Arg Ala Glu Ser Asp Glu     (SEQ ID NO:9)

Ala Arg Arg Cys Tyr Asn Asp Pro Lys

Cys Cys Asp Phe Val Thr Asn Arg Gly

Ala Cys 2-2. Synthesis of an Adsorbent (Kac-SEQ ID NO:9)

To 90 ml of our prototype cellulosic porous hard gel Kac having a spherical protein molecular weight exclusion limit of 5,000,000 was added sufficient water to make 180 ml, followed by 60 ml of 2M sodium hydroxide, then the temperature was adjusted to 40° C. To this was added 21 ml of epichlorohydrin, and the reaction was carried out at 40° C. with stirring for 1 hour. After completion of the reaction, the product was rinsed with water thoroughly to give an epoxy-activated cellulose gel.

In 0.5 mL of 0.05 M borate buffer (pH 10.0) was dissolved 2 mg of the peptide (SEQ ID NO:9) synthesized under 2-1., and the solution was readjusted to pH 10 and made up to 1.0 mL(peptide solution) with 0.01 N sodium hydroxide/$H_2O$ solution. This peptide solution was added to 0.4 mL of the above epoxy-activated Kac and after the mixture was shaken at 37° C. for 16 hours, the product was washed with a sufficient quantity of PBS (10 mM phosphate buffer containing 150 mM sodium chloride) to give Kac-SEQ ID NO:9.

The immobilization rate determined in the same manner as under 1-2-2. was 3.2 mg/mL (0.8 μmol/ml) for Kac-SEQ ID NO:9.

2-3. Evaluation of the Adsorbent

Except that Kac-SEQ ID NO:9 was used in lieu of the GCL2000m-SEQ ID NO:4 used in Example 1 (1-3.) and DCM patient serum B (β1AR-Ab(+)) in lieu of DCM patient serum A, the adsorption experiment, ELISA, absorbance measurement and adsorptive capacity calculation were performed otherwise in the same way as in Example 1 (1-3.) (See Table 1 for results).

EXAMPLE 3

3-1. The Following Peptide (SEQ ID:10) was Synthesized in Exactly the Same Way as Described in Example 1(1-1.).

Val Arg Thr Val Glu Asp Gly Glu Cys  (SEQ ID NO:10)

Tyr Ile Gln Phe Phe Ser Asn Ala Ala

Val Thr Phe Gly Thr Ala Ile Pro Ala

Lys Lys

In addition, for preparation of a peptide solution for use in ELISA, the following peptide was also synthesized inexactly the same way as described in Example 1 (1-1.).

Val Arg Thr Val Glu Asp Gly Glu Cys Tyr

Ile Gln Phe Phe Ser Asn Ala Ala Val Thr

Phe Gly Thr Ala Ile (M2R)

3-2. Synthesis of an Adsorbent (Eu-SEQ ID NO:10)

The epoxy-activated methacrylamide polymer Eupergit C 250 L (molecular weight exclusion limit of 1,000,000, product of Rohm Pharma) was swollen with 0.05 M borate buffer (pH 10.0) for 15 minutes and washed with 0.05 M borate buffer (pH 10.0). In 0.5 mL of 0.05 M borate buffer (pH10.0) was dissolved 10 mg of the peptide (SEQ ID NO:10) synthesized under 3-1., and the solution was readjusted to pH 10 and made up to 1.0 mL(peptide solution) by adding 0.01 N sodium hydroxide/$H_2O$ solution. This solution was admixed with 0.4 mL of the pretreated Eupergit C 250 L and after the mixture was shaken at 37° C. for 16 hours, it was washed with a sufficient quantity of PBS (10 mM phosphate buffer containing 150 mM sodium chloride) to give Eu-SEQ ID NO:10.

The immobilization rate determined in the same manner as described under 1-2-2. was 15 mg/mL (4.09 μmol/mL) for Eu-SEQ ID NO:10.

3-3. Evaluation of the Adsorbent

Except that Eu-SEQ ID NO:10 was used in lieu of the GCL2000m-SEQ ID NO:4 used in Example 1 (1-3.), the antibody against M2 muscarinic receptor-positive (briefly, M2R-Ab(+)) DCM patient serum C in lieu of DCM patient serum A and that M2R was used in lieu of β1AR2nd as the peptide to be dissolved for making the peptide solution to be first added to an ELISA plate, the adsorption experiment, ELISA, absorbance measurement, and adsorptive capacity calculation were carried out in otherwise the same manner as in Example 1(1-3.) (See Table 1 for the result).

EXAMPLE 4

4-1. The Following Peptides (SEQ ID NOS:11,12) were Synthesized in Exactly the Same Manner as Described in Example 1 (1-1.).

His Trp Trp Arg Ala Glu Ser Asp Glu  (SEQ ID NO:11)

Ala Arg Arg Cys Tyr Asn Asp Pro Lys

Cys Cys Asp Phe Val Thr Asn Arg Ala

Cys

Val Arg Thr Val Glu Asp Gly Glu Cys  (SEQ ID NO:12)

Tyr Ile Gln Phe Phe Ser Asn Ala Ala

Val Thr Phe Gly Thr Ala Ile Cys 4-2. Synthesis of an Adsorbent (Kac-SEQ ID NOS:11,12)

The peptides synthesized under 4-1.(SEQ ID NO:11, 2.5 mg; SEQ ID NO:12, 3 mg) were dissolved in 0.5 mL of 0.05 M borate buffer (pH 10.0) and the solution was readjusted to pH 10 and made up to a total of 1.0 mL(peptide solution) by adding 0.01 N sodium hydroxide/$H_2O$ solution. This peptide solution was added to 0.4 mL of the epoxy-activated Kac synthesized in Example 2 (2-2.) and after the mixture was shaken at 37° C. for 16 hours, it was washed with a sufficient quantity of PBS (10 mM phosphate buffer containing 150 mM sodium chloride) to give Kac-SEQ ID NOS:11,12.

The immobilization rates determined in the same manner as under 1-2-2. were 2 mg/mL (0.51 μmol/ml) for Kac-SEQ ID NO:11, and 2 mg/mL (0.61 μmol/ml) for Kac-SEQ ID NO:12.

4-3. Evaluation of the Adsorbent

Except that Kac-SEQ ID NOS:11,12 was used in lieu of the GCL2000m-SEQ ID NO:4 used in Example 1 (1-3.) and DCM patient serum D (β1AR-Ab(+)) in lieu of DCM patient serum A, the adsorption experiment, ELISA, absorbance measurement, and adsorptive capacity calculation were carried out in otherwise the same manner as in Example 1 (1-3.). (See Table 1 for the result)

EXAMPLE 5

5-1. The Following Peptide (SEQ ID NO:13) was Synthesized in Exactly the Same Manner as Described in Example 1(1-1.).

Ser Phe Phe Cys Glu Leu Ala Asp Gly  (SEQ ID NO:13)

Tyr Pro Lys Cys Cys Asp Phe Ala Cys 5-2. Synthesis of an Adsorbent (Kac-SEQ ID NO:13)

In 0.5 mL of 0.05 M borate buffer (pH 10.0) was dissolved 3 mg of the peptide (SEQ ID NO:13) synthesized under 5-1., and the solution was readjusted to pH 10 and made up to a total of 1.0 mL(peptide solution) by adding sufficient 0.01 N sodium hydroxide/$H_2O$. This peptide solution was added to 0.4 mL of the epoxy-activated Kac synthesized in Example 2 (2-2.) and after the mixture was shaken at 37° C. for 16 hours, the product was washed with a sufficient quantity of PBS (10 mM phosphate buffer containing 150 mM sodium chloride) to give Kac-SEQ ID NO:13.

The immobilization rate determined in the same manner as described under 1-2-2. was 3.4 mg/mL (1.46 μmol/ml) for Kac-SEQ ID NO:13.

5-3. Evaluation of the Adsorbent

Except that Kac-SEQ ID NO:13 was used in lieu of the GCL2000m-SEQ ID NO:4 used in Example 1 (1-3.) and DCM patient serum D (β1AR-Ab(+)) in lieu of DCM patient serum A, the adsorption experiment, ELISA, absorbance measurement, and adsorptive capacity calculation were carried out in otherwise the same manner as in Example 1 (1-3.). (See Table 1 for the result)

EXAMPLE 6

To 1 mL of the adsorbent Kac-SEQ ID NO:13 synthesized in Example 5 (5-2.) (or 1 mL of Kac for blank test) was added 6 mL of healthy human serum (β1AR-Ab(−), M2R-Ab(−)), and after the mixture was shaken at 37° C. for 2 hours, the albumin concentration, IgG concentration, and IgM concentration of the supernatant were determined (Shionogi Biomedical Laboratories was requested to carry out the assay). The adsorption rates calculated for the adsorbent Kac-SEQ ID NO:13 with each concentration in the blank test being taken as 0% adsorption are shown in Table 2.

TABLE 1

| | Abbreviation of adsorbent | Adsorptive capacity |
|---|---|---|
| Example 1 | GCL2000m - SEQ ID NO: 4 | 35% |
| Comparative Example 1 | Sepharose 4B - β 1AR2nd | 15% |
| Example 2 | Kac - SEQ ID NO: 9 | 70% |
| Example 3 | Eu - SEQ ID NO: 10 | 60% |
| Example 4 | Kac - SEQ ID NOS: 11, 12 | 80% |
| Example 5 | Kac - SEQ ID NO: 13 | 70% |

TABLE 2

| Measurement item | Adsorption rate |
|---|---|
| Albumin | <5% |
| IgG | <5% |
| IgM | <5% |

INDUSTRIAL APPLICABILITY

In accordance with the present invention, as can be understood from the above Examples, there is provided a novel adsorbent adapted to selectively adsorb an antibody against β1-adrenoceptor and/or an antibody against M2 muscarinic receptor occurring in a body fluid. Moreover, by means of a body fluid treatment apparatus packed with said adsorbent, an antibody against β1-adrenoceptor and/or an antibody against M2 muscarinic receptor in an untreated fluid, such as blood, plasma or serum, can be selectively removed.

The invention claimed is:

1. An adsorbent for an antibody against β1-adrenoceptor and/or an antibody against M2 muscarinic receptor which comprises a water-insoluble carrier, and a compound having a binding affinity for an antibody against β1-adrenoceptor and/or an antibody against M2 muscarinic receptor, in which said compound is immobilized on the water-insoluble carrier, and in which said compound having a binding affinity for an antibody against β1-adrenoceptor and/or an antibody against M2 muscarinic receptor is at least one peptide selected from the group consisting of Trp Gly Arg Trp Glu Tyr Gly Ser Phe Phe Cys Glu Leu (SEQ ID NO: 1), Glu Tyr Gly Ser Phe Phe (SEQ ID NO:2), Ser Phe Phe Cys Glu Leu (SEQ ID NO:3), Arg Ala Glu Ser Asp Glu Ala Arg Arg Cys Tyr Asn Asp Pro Lys Cys Cys Asp Phe Val Thr Asn Arg (SEQ ID NO:4),
Val Lys Ala Phe His Arg Glu Leu Val Pro Asp (SEQ ID NO:5),
Ala Arg Arg Cys Tyr Asn Asp (SEQ ID NO:6),
Pro Lys Cys Cys Asp Phe (SEQ ID NO:7), and
Val Arg Thr Val Glu Asp Gly Glu Cys Tyr Ile Gln Phe Phe Ser Asn Ala Ala Val Thr Phe Gly Thr Ala Ile (SEQ ID NO:8).

2. An adsorbent for an antibody against β1-adrenoceptor and/or an antibody against M2 muscarinic receptor,
  which comprises a water-insoluble carrier, and a compound having a binding affinity for an antibody against β1-adrenoceptor and/or an antibody against M2 muscarinic receptor,
  in which said compound is immobilized on the water-insoluble carrier, and
  in which the compound having a binding affinity for an antibody against β1-adrenoceptor and/or an antibody against M2 muscarinic receptor is at least one peptide selected from the group consisting of

```
X Trp Gly Arg Trp Glu Tyr Gly Ser Phe Phe Cys Glu Leu Y,    (SEQ ID NO:1a)

X Glu Tyr Gly Ser Phe Phe Y,                                 (SEQ ID NO:2a)

X Ser Phe Phe Cys Glu Leu Y,                                 (SEQ ID NO:3a)

X His Trp Trp Arg Ala Glu Ser Asp Glu Ala Arg Arg Cys Tyr    (SEQ ID NO:4a)
Asn Asp Pro Lys Cys Cys Asp Phe Val Thr Asn Arg Y,

X Val Lys Ala Phe His Arg Glu Leu Val Pro Asp Y,             (SEQ ID NO:5a)

X Ala Arg Arg Cys Tyr Asn Asp Y,                             (SEQ ID NO:6a)

X Pro Lys Cys Cys Asp Phe Y,                                 (SEQ ID NO:7a) and

X Val Arg Thr Val Glu Asp Gly Glu Cys Tyr Ile Gln Phe Phe    (SEQ ID NO:8a)
Ser Asn Ala Ala Val Thr Phe Gly Thr Ala Ile Y,
``` in which Y represents Gly-Ala-Cys, or Ala-Cys, or Cys.

3. An adsorbent for an antibody against β1-adrenoceptor and/or an antibody against M2 muscarinic receptor,
  which comprises a water-insoluble carrier, and a compound having a binding affinity for an antibody against β1-adrenoceptor and/or an antibody against M2 muscarinic receptor,
  in which said compound is immobilized on the water-insoluble carrier, and
  in which the compound having a binding affinity for an antibody against β1-adrenoceptor and/or an antibody against M2 muscarine receptor is a peptide comprising a linear peptide formed by coupling two or more peptides selected from the group consisting of
Trp Gly Arg Trp Glu Tyr Gly Ser Phe Phe Cys Glu Leu (SEQ ID NO: 1),
Glu Tyr Gly Ser Phe Phe (SEQ ID NO:2),
Ser Phe Phe Cys Glu Leu (SEQ ID NO:3),
Arg Ala Glu Ser Asp Glu Ala Arg Arg Cys Tyr Asn Asp Pro Lys Cys Cys Asp Phe Val Thr Asn Arg (SEQ ID NO:4),
Val Lys Ala Phe His Arg Glu Leu Val Pro Asp (SEQ ID NO:5),
Ala Arg Arg Cys Tyr Asn Asp (SEQ ID NO:6),
Pro Lys Cys Cys Asp Phe (SEQ ID NO:7), and
Val Arg Thr Val Glu Asp Gly Glu Cys Tyr Ile Gln Phe Phe Ser Asn Ala Ala Val Thr Phe Gly Thr Ala Ile (SEQ ID NO:8) with a peptide consisting of Ala-Asp-Gly-Tyr,
  wherein the peptide consisting of Ala-Asp-Gly-Tyr is located between the two or more peptides that form the linear peptide, and
  a peptide having Ala-Cys at the C-terminus of said linear peptide.

4. The adsorbent for an antibody against β1-adrenoceptor and/or an antibody against M2 muscarinic receptor according to any of claims 1, 2, or 3, wherein the compound having a binding affinity for an antibody against β1-adrenoceptor and/or an antibody against M2 muscarinic receptor is immobilized on the water-insoluble carrier in a proportion of 0.00001 μmol to 100 μmol per mL of the carrier.

5. The adsorbent for an antibody against β1-adrenoceptor and/or an antibody against M2 muscarinic receptor according to any of claims 1, 2, or 3, wherein said water-insoluble carrier is porous.

6. The adsorbent for an antibody against β1-adrenoceptor and/or an antibody against M2 muscarinic receptor according to claim 5, wherein said water-insoluble carrier has a molecular weight exclusion limit of 150,000 to 10,000,000.

7. The adsorbent for an antibody against β1-adrenoceptor and/or an antibody against M2 muscarinic receptor according to any of claims 1, 2, or 3, wherein said water-insoluble carrier is hydrophilic.

8. An adsorption apparatus for adsorbing an antibody against β1-adrenoceptor and/or an antibody against M2 muscarinic receptor which comprises:
  a housing equipped with a liquid inlet and a liquid outlet and packed with the adsorbent according to any of claims 1, 2, or 3, and
  a means for preventing emigration of said adsorbent from the housing.

9. A method of adsorbing an antibody against β1-adrenoceptor and/or an antibody against M2 muscarinic receptor which comprises a step of contacting the adsorbent according to any of claims 1, 2, or 3 with a fluid containing an antibody against β1-adrenoceptor and/or an antibody against M2 muscarinic receptor.

10. The method according to claim 9, wherein said fluid containing an antibody against β1-adrenoceptor and/or an antibody against M2 muscarinic receptor is a body fluid.

11. The method according to claim 10, which comprises adsorbing an immunocomplex comprising an antibody against β1-adrenoceptor and/or an antibody against M2 muscarinic receptor occurring in a body fluid as a component.

* * * * *

UNITED STATES PATENT AND TRADEMARK OFFICE
CERTIFICATE OF CORRECTION

| | |
|---|---|
| PATENT NO. | : 7,309,488 B2 |
| APPLICATION NO. | : 10/221042 |
| DATED | : December 18, 2007 |
| INVENTOR(S) | : Eiji Ogino et al. |

It is certified that error appears in the above-identified patent and that said Letters Patent is hereby corrected as shown below:

<u>Col. 23</u>

Line 24, replace "X Trp" with --Trp--;

Line 25, replace "X Glu" with --Glu--;

Line 26, replace "X Ser" with --Ser--;

Line 27, replace "X His" with --His--;

Line 28, replace "X Val" with --Val--;

Line 29, replace "X Ala Arg Arg Cys Tyr Asn Asp Y, (SEQ ID NO:6a)" with --Ala Arg Arg Cys Tyr Asn Asp Y, (SEQ ID NO:6a) and--;

Line 30, replace "X Pro Lys Cys Cys Asp Phe Y, (SEQ ID NO:7a) and" with --Pro Lys Cys Cys Asp Phe Y, (SEQ ID NO:7a)--;

Line 31, delete "X Val Arg Thr Val Glu Asp Gly Glu Cys Tyr Ile Gln Phe Phe (SEQ ID NO:8a)"; and Line 32, delete "Ser Asn Ala Ala Val Thr Phe Gly Thr Ala Ile Y,".

Line 65, replace "Tyr lie" with --Tyr Ile--; and

UNITED STATES PATENT AND TRADEMARK OFFICE
CERTIFICATE OF CORRECTION

| | |
|---|---|
| PATENT NO. | : 7,309,488 B2 |
| APPLICATION NO. | : 10/221042 |
| DATED | : December 18, 2007 |
| INVENTOR(S) | : Eiji Ogino et al. |

It is certified that error appears in the above-identified patent and that said Letters Patent is hereby corrected as shown below:

Col. 23

Line 66, replace "Ala Ile" with --Ala Ile--.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO.        : 7,309,488 B2
APPLICATION NO.   : 10/221042
DATED             : December 18, 2007
INVENTOR(S)       : Eiji Ogino et al.

It is certified that error appears in the above-identified patent and that said Letters Patent is hereby corrected as shown below:

Col. 23

Line 13, replace "X Trp" with --Trp--;

Line 14, replace "X Glu" with --Glu--;

Line 15, replace "X Ser" with --Ser--;

Line 16, replace "X His" with --His--;

Line 18, replace "X Val" with --Val--;

Line 19, replace "X Ala Arg Arg Cys Tyr Asn Asp Y, (SEQ ID NO:6a)" with --Ala Arg Arg Cys Tyr Asn Asp Y, (SEQ ID NO:6a) and--;

Line 20, replace "X Pro Lys Cys Cys Asp Phe Y, (SEQ ID NO:7a) and" with --Pro Lys Cys Cys Asp Phe Y, (SEQ ID NO:7a)--;

Line 21, delete "X Val Arg Thr Val Glu Asp Gly Glu Cys Tyr Ile Gln Phe Phe (SEQ ID NO:8a)"; and Line 22, delete "Ser Asn Ala Ala Val Thr Phe Gly Thr Ala Ile Y,".

Line 25, replace "Tyr lie" with --Tyr Ile--; and

Line 26, replace "Ala lie" with --Ala Ile--.

This certificate supersedes the Certificate of Correction issued October 27, 2009.

Signed and Sealed this

Twelfth Day of January, 2010

David J. Kappos
*Director of the United States Patent and Trademark Office*